United States Patent [19]

Vecchietti et al.

[11] Patent Number: 5,366,981
[45] Date of Patent: Nov. 22, 1994

[54] N-ACYL-SUBSTITUTED AZACYCLIC COMPOUNDS, PROCESSES FOR THEIR PREPARAION, AND THEIR USE AS PHARMACEUTICALS

[75] Inventors: Vittorio Vecchietti; Roberto Colle; Giulio Dondio; Giuseppe Giardina, all of Milan, Italy

[73] Assignee: Dr Lo Zambeletti S.p.A., Milan, Italy

[21] Appl. No.: 859,389

[22] PCT Filed: Nov. 14, 1990

[86] PCT No.: PCT/EP90/01961

§ 371 Date: May 22, 1992

§ 102(e) Date: May 22, 1992

[87] PCT Pub. No.: WO91/08205

PCT Pub. Date: Jun. 13, 1991

[30] Foreign Application Priority Data

Nov. 24, 1989 [GB] United Kingdom ................. 8926560

[51] Int. Cl.$^5$ ................. C07D 401/06; C07D 495/04; A61K 31/47; A61K 31/445
[52] U.S. Cl. ........................... 514/301; 514/307; 514/319; 514/326; 546/114; 546/146; 546/205; 546/206; 546/208
[58] Field of Search ............... 546/114, 146, 205, 206, 546/208; 514/301, 307, 319, 330, 326

[56] References Cited

U.S. PATENT DOCUMENTS

| | | | |
|---|---|---|---|
| 4,753,952 | 6/1988 | Vecchietti | 514/307 |
| 4,826,819 | 5/1989 | Vecchietti | 514/212 |
| 4,879,300 | 11/1989 | Giordani | 514/317 |
| 4,954,509 | 9/1990 | Vecchietti | 546/143 |
| 4,994,450 | 2/1991 | Vecchietti | 514/183 |
| 4,999,359 | 3/1991 | Vecchietti | 514/301 |
| 5,030,649 | 7/1991 | Vecchietti | 548/568 |
| 5,041,451 | 8/1991 | Colle | 514/301 |
| 5,087,630 | 2/1992 | Colle | 514/307 |
| 5,089,507 | 2/1992 | Vecchietti | 546/227 |
| 5,254,564 | 10/1993 | Vecchietti | 514/307 |

FOREIGN PATENT DOCUMENTS

| | | |
|---|---|---|
| 0232612 | 12/1986 | European Pat. Off. . |
| 0232989 | 1/1987 | European Pat. Off. . |
| 0330360 | 2/1989 | European Pat. Off. . |
| 0330461 | 2/1989 | European Pat. Off. . |
| 0330467 | 2/1989 | European Pat. Off. . |
| 0330469 | 2/1989 | European Pat. Off. . |
| 0366327 | 10/1989 | European Pat. Off. . |
| 0447704A1 | 3/1990 | European Pat. Off. . |
| 0374756 | 6/1990 | European Pat. Off. . |
| WO91/17116 | 11/1991 | WIPO . |
| WO92/15304 | 9/1992 | WIPO . |
| WO92/15592 | 9/1993 | WIPO . |

OTHER PUBLICATIONS

U.S. patent application Ser. No. 07/859,388, Colle et al., May 22, 1992.

Mukaiyama, et al., "Enantioface-Differentiating (Asymmetric) Addition of Alkyllithium and Dialkylmagnesium to Aldehydes by Using (2S,2'S)-2-Hydroxymethyl-1-((1-alkylpyrrolidin-2-yl)-methyl)pyrrolidines as Chiral Ligands", J. Am. Chem. Soc., vol. 101, No. 6, 1979, pp. 1455–1460.

Gottschlich et al., "Preparation of 2-acyl-1-Pyrrolidinomethyl)-1,2,3,4-tetrahydroisoquinolines and analogs as drugs", CA 113:211862x (1990).

Brooks et al., Opiate Receptors with the Blood–Brain Barrier Mediate Kappa Agonist–Induced Water Diuresis, J. Pharmacol. Exp. Ther., 266, 164 (1993).

Silvia et al., Protection from ischemia–induced cerebral edema in the rat by U–50488H, a kappa opioid receptor agonist, Brain Res., 403, 52 (1987).

Hall et al., Stroke, Quantitative Analysis of Effects of k-Opioid Agonists on Postischemic Hippocampal CA1 Neuronal Necrosis in Gerbils, 19, 8 1008 (1988).

Primary Examiner—Marianne M. Cintins
Assistant Examiner—Phyllis G. Spivack
Attorney, Agent, or Firm—Charles M. Kinzig; Stephen Venetianer; Edward T. Lentz

[57] ABSTRACT

A compound, a solvate or salt thereof, of formula (I):

(Abstract continued on next page.)

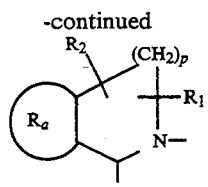

(I)

in which:
A is

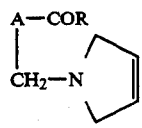

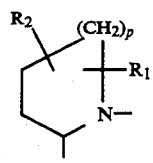

or

-continued p is 2;

ROC— is an acyl group linked to a substituted or unsubstituted carbocyclic aromatic ring system;

$R_1$ and $R_2$ are substituents on the same or different carbon atoms and are independently hydrogen or $C_{1-6}$ alkyl; and $R_a$ is a phenyl or thienyl ring, and is useful for the treatment of pain, hyponatremic disease states or cerebral ischemia.

13 Claims, No Drawings

N-ACYL-SUBSTITUTED AZACYCLIC COMPOUNDS, PROCESSES FOR THEIR PREPARAION, AND THEIR USE AS PHARMACEUTICALS

This invention is concerned with novel substituted azacyclic compounds, processes for their preparation, and their use in medicine, particularly as analgesics.

Compounds which are kappa-receptor agonists act as analgesics through interaction with kappa opioid receptors. The advantage of kappa-receptor agonists over the classical μ-receptor agonists, such as morphine, lies in their ability to cause analgesia while being devoid of morphine-like behavioural effects and addiction liability.

European Published Patent Applications No. 0232612, discloses a group of azacyclic derivatives which exhibit kappa-receptor agonism without some of the behavioural effects of morphine and morphine analogues, and which are thus of potential therapeutic utility as analgesics.

A novel class of substituted azacyclic compounds has now been discovered which also exhibit potent kappa-receptor agonism without the aforementioned undesirable behavioural effects.

The novel class of compounds also possess diuretic activity which indicates that they are of potential use in the treatment of hyponatraemic disease states in mammals. The compounds are also of potential use in the treatment of cerebral ischaemia.

According to the present invention there is provided a compound, or a solvate or salt thereof, of formula (I):

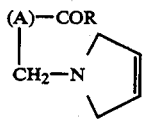

(I)

in which:
(A) is

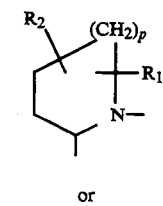

or

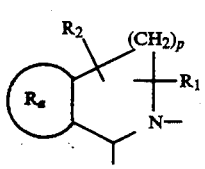

p is 1, 2 or 3;
ROC— is an acyl group linked to the nitrogen atom of group (A) in which the group R contains a substituted or unsubstituted carbocyclic aromatic or heterocyclic aromatic ring;
$R_1$ and $R_2$ are substituents on the same or different carbon atoms and are independently hydrogen or $C_{1-6}$ alkyl;
$R_a$ is a fused substituted or unsubstituted heterocyclic or carbocyclic aromatic ring.

The $C_{1-6}$ alkyl groups of $R_1$ and $R_2$ may be either straight or branched chain and examples are methyl, ethyl, propyl, n-butyl, n-pentyl or n-hexyl. $R_1$ and $R_2$ are preferably hydrogen or methyl, especially gem-dimethyl.

In (A), p is preferably 2 so that (A) has the character of a piperidine ring.

In the definition of ROC— the term "carbocyclic aromatic" includes single or fused rings, having 6 to 12 ring carbon atoms, and the term "heterocyclic aromatic" includes single or fused rings having 5 to 12 ring atoms, comprising up to four hetero-atoms in the or each ring, selected from oxygen, nitrogen and sulphur. When the carbocyclic or heterocyclic group is a fused two ring system, one or both rings may be aromatic in character. Suitably, one of the rings is aromatic and the other is non-aromatic.

When $R_a$ forms a heterocyclic group, it may be a single ring having aromatic character, containing up to 6 ring atoms and comprising up to 2 hetero-atoms in the ring selected from oxygen, nitrogen and sulphur.

When $R_a$ forms an optionally substituted phenyl ring, examples of substituents are one or more of $C_{1-6}$ alkyl, preferably methyl, halogen,, hydroxy, $C_{1-6}$ alkoxy, thiol or $C_{1-6}$ alkyl thio. Suitably $R_x$ represents thienyl, imidazolyl and unsubstituted phenyl.

The group R preferably has the formula (II):

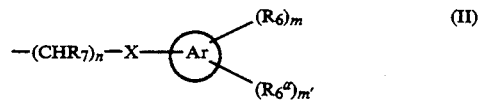

(II)

in which
n is 0, 1 or 2;
m is 0, 1 or 2;
m' is 0, 1 or 2, provided $m+m' \leq 2$
X is a direct bond, or O, S or $NR_8$ in which $R_8$ is hydrogen or $C_{1-6}$ alkyl,
Ar is a substituted or unsubstituted carbocyclic or heterocyclic group,
each of $R_6$ and $R_6{}^a$ is $C_{1-6}$ alkyl, $C_{2-6}$ alkenyl, $C_{2-6}$ alkynyl, $C_{1-6}$ haloalkyl, $C_{2-6}$ haloalkenyl, $C_{2-6}$ haloalkynyl, optionally substituted phenyl, optionally substituted phenyl $C_{1-6}$ alkyl, hydroxy, $C_{1-6}$ alkoxy, thiol, $C_{1-6}$ alkylthio, $C_{1-6}$ haloalkoxy, $C_{1-6}$ haloalkylthio, halogen, $NO_2$, CN, $CF_3$, —$OCF_3$, —$OCHF_2$, —$OCF_2CF_2H$, —$OCCl_2CF_3$, —$COOR_9$, —$CONR_{10}R_{11}$, —$SO_3R_{12}$, —$SO_2NR_{13}R_{14}$ and —$COR_{15}$ in which each of $R_9$ to $R_{15}$ is independently hydrogen, $C_{1-6}$ alkyl, optionally substituted phenyl or optionally substituted phenyl $C_{1-6}$ alkyl;
or, when m is 2 and m' is 0, two $R_6$'s form a $C_{3-6}$ polymethylene group, and $R_7$ is hydrogen or $C_{1-6}$ alkyl, such as methyl or ethyl.

Preferred halogens are F, Cl and Br.

When two $R_6$'s are linked they preferably form a fused cyclopentyl or cyclohexyl ring.

Preferably Ar is phenyl and $R_6$ or $R_6{}^a$ is preferably in the meta and/or para position.

Preferably $R_6$ or $R_6{}^a$ is bromine, chlorine, or $CF_3$, particularly in the meta- or para-position.

X is typically oxygen or a direct bond, and n is typically 0 or 1.

A further preferred group R has the formula (IIa)

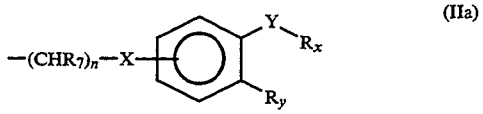
(IIa)

in which the group —(CHR$_7$)$_n$—X—, which is as defined in formula II, is in the meta- or para-position with respect to YR$_x$ or R$_y$, Y is >C=O, >CHOH, >S=O or >SO$_2$;

each of R$_x$ and R$_y$ is C$_{1-6}$ alkyl, or

R$_x$ and R$_y$ are linked together and R$_x$ represents —(Z-)$_m$— where m is 0 or 1 and Z is O, S or NR$_z$ where R$_z$ is hydrogen or C$_{1-6}$ alkyl, and R$_y$ represents —(CH$_2$)$_q$— where q is an integer of from 1 to 4, preferably 2 or 3.

A preferred sub-group of formula (IIa) is a group of formula (IIb)

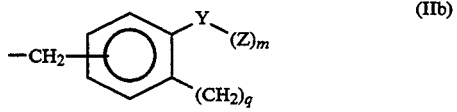
(IIb)

in which Y, Z, m, q and the position of —CH$_2$— are as defined in formula (IIa).

Preferably, q is 2 when Z is oxygen and m is 1, and q is 3 when m is 0.

A further preferred sub-group of formula (IIa) is the group of formula (IIc)

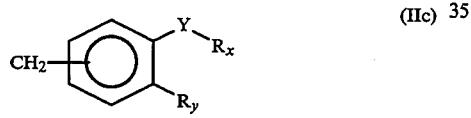
(IIc)

in which Y is >C=O or CHOH, each of R$_x$ and R$_y$ is C$_{1-6}$ alkyl, preferably methyl, and the position of —CH$_2$— is as defined in formula (IIa)

Some typical examples of suitable R substituents are

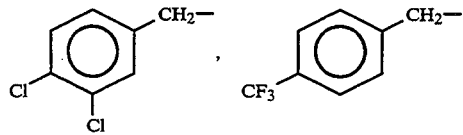

The compounds of formula I or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula I or its salt or solvate.

One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula I include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

Examples of a pharmaceutically acceptable solvate of a compound of formula I include the hydrate.

The compounds of formula I have at least one asymmetric center and therefore exist in more than one stereoisomeric form. The invention extends to all such forms and to mixtures thereof, including racemates.

The present invention also provides a process for the preparation of a compound of formula (I) which comprises reacting a compound of formula (III):

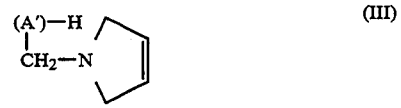
(III)

in which
(A') is

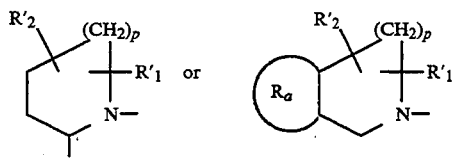

in which
R$_1$' and R$_2$' are R$_1$ and R$_2$ respectively as defined for formula (I), or each is a group or atom convertible to R$_1$ or R$_2$ respectively, and p is 1, 2 or 3.

with a compound of formula R'CO.OH or an active derivative thereof, in which R' is R as defined for formula (I), or a group convertible to R, to form a compound of formula (I'):

(I')

and then optionally performing one of the following steps:

a) where R', R$_1$' and R$_2$' are other than R, R$_1$ and R$_2$, converting R', R$_1$' and R$_2$' to R, R$_1$ and R$_2$ to obtain a compound of formula (I), b) where R', R$_1$' and R$_2$' are R, R$_1$ and R$_2$ converting one R, R$_1$ or R$_2$ to another R, R$_1$ or R$_2$ to obtain a compound of formula (I), c) forming a salt and/or solvate of the obtained compound of formula (I) .

Suitable active derivatives of R'CO.OH are acid chlorides or acid anhydrides. Another suitable derivative is a mixed anhydride formed between the acid and an alkyl chloroformate.

For example, in standard methods well known to those skilled in the art, the compound of formula (III) may be coupled:

a) with an acid chloride in the presence of an inorganic or organic base,
b) with the acid in the presence of dicyclohexyl carbodiimide, N-dimethylaminopropyl-N'-ethyl carbodiimide or carbonyl diimidazole,
c) with a mixed anhydride generated in situ from the acid and an alkyl (for example ethyl) chloroformate.

It will be appreciated that a compound of formula (I') may be converted to a compound of formula (I), or one compound of formula (I) may be converted to another compound of formula (I), by interconversion of suitable substituents. Thus certain compounds of formula (I) and (I') are useful intermediates in forming other compounds of the present invention.

$R_1'$ and $R_2'$ are preferably $R_1$ and $R_2$ respectively.

The above described process can provide a diastereoisomeric mixture which can be subsequently separated into isomers by column chromatography. The compound R'CO.OH is typically of the formula (IId):

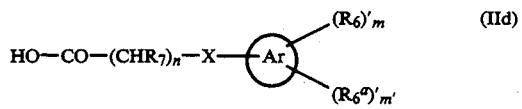

in which $R_6'$ is $R_6$ and $(R_6^a)'$ is $R_6^a$ are as defined for formula (II), or a group or atom convertible to $R_6$ or $R_6^a$, the other variables being as defined for formula (II).

Conversions of substituents $R_6'$ or $(R_6^a)'$ on the aromatic group (AR) to obtain $R_6$ or $R_6^a$ are generally known in the art of aromatic chemistry. $R_6'$ is preferably $R_6$ and $(R_6^a)'$ is preferably $R_6^a$.

A preferred reagent is the equivalent acid halide of formula (IId) in which the halide is typically chlorine or bromine.

The compounds of formula (I) may be converted into their pharmaceutically acceptable acid addition salts by reaction with the appropriate organic or mineral acids.

Solvates of the compounds of formula (I) may be formed by crystallization or recrystallization from the appropriate solvent. For example hydrates may be formed by crystallization or recrystallization from aqueous solutions, or solutions in organic solvents containing water.

Also salts or solvates of the compounds of formula (I) which are not pharmaceutically acceptable may be useful as intermediates in the production of pharmaceutically acceptable salts or solvates. Accordingly such salts or solvates also form part of this invention.

The compounds of formula (I) and their intermediates exist in more than one stereoisomeric form and the processes of the invention produces mixtures thereof. The individual enantiomers may be obtained by resolution of the compounds of formula (I) using an optically active acid such as tartaric acid or by resolution of the intermediate diamines of formula (III), for example by first protecting the NH group with an alkyl or benzyl chloroformate, resolving the compound thus formed using an active acid, such as O,O'di-p-toluoyl tartaric acid, and subsequently deprotecting the optically active alkyl or benzyl carbamates in accordance with standard methods.

Alternatively, compounds of formula (III) may be treated with an optically active acid chloride, such as S(−)-camphanic chloride, and the pure enantiomers can be obtained by hydrolysis of the separated diastereomeric amides.

Alternatively, an asymmetric synthesis would offer a route to individual enantiomers.

The compounds of formula (III) may be conveniently prepared by reduction of a compound of formula (IV):

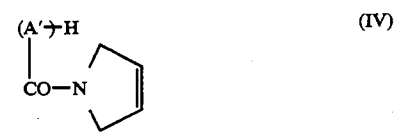

The compounds of formula (IV) may be obtained by reaction of an N-carbethoxy-protected amino acid of formula (V):

firstly with thionyl chloride, then with 3-pyrroline.

The overall reaction from (V) to (III) is illustrated in the following reaction scheme I:

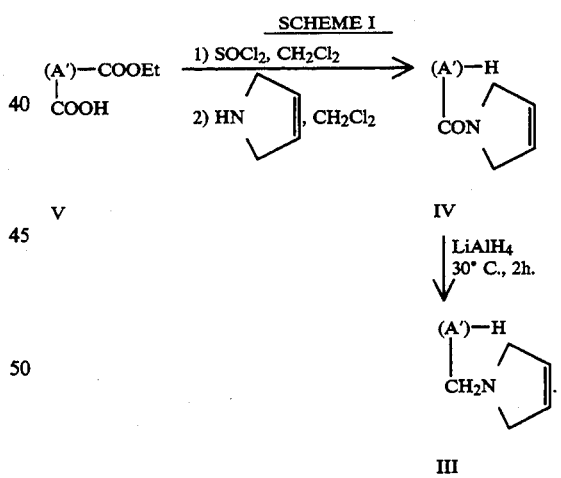

The reactions with thionyl chloride and 3-pyrroline both conveniently take place in dichloromethane as solvent. A low temperature of about −5° C. is preferably used. The subsequent reduction preferably uses a mixed hydride such as LiAlH$_4$ in an inert solvent, preferably THF. A temperature of about 30° C. and reaction time of about 2 hours, have been found to give good results.

The compounds of formula (III) in which (A) includes the fused ring system $R_a$ may also be obtained by reacting pyrroline with a compound of formula (VI):

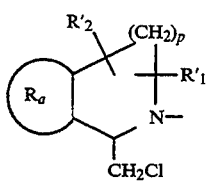

The resultant compound of formula (VII):

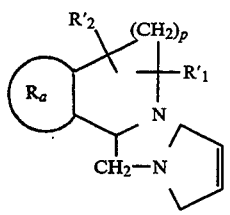

is then reduced to a compound of formula (III).

This route is summarised in the following reaction scheme II:

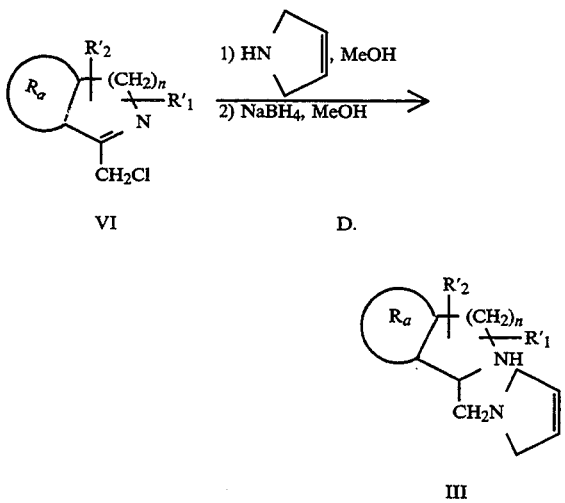

In this scheme, the reaction with pyrroline may take place in a suitable solvent, such as methanol, typically at 0° to 50° C. The reduction of the resulting intermediate may be carried out with a mixed hydride such as $NaBH_4$ or $NaCNBH_3$, preferably in a protic solvent, again conveniently methanol.

The compounds of formulae (V) and (VI) are known compounds or can be prepared by routine methods from known compounds. Reference is directed to European Published Patent Application No. 0232989 previously cited.

The intermediate compounds of formula (III) above are novel compounds and, as such, they form a further aspect of this invention.

The activity of the compounds of formula (I) in standard tests indicates that they are of potential therapeutic utility in the treatment of pain, hyponatraemic disease states, and cerebral ischaemia.

Accordingly the present invention also provides a compound of formula (I), or a pharmaceutically acceptable salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of pain, hyponatraemic diseases states, or cerebral ischaemia.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents diuretics, or agents for treating cerebral ischaemia.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain or as a diuretic, or for treatment of cerebral ischaemia.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinyl-pyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

As mentioned earlier, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

Within the above indicated dosage range, no adverse toxicological effects have been observed with compounds of the invention.

The present invention also provides a method for the treatment and/or prophylaxis of pain and/or hyponatraemic disease states and/or cerebral ischaemia in mammals, particularly humans, which comprises administering to the mammal in need of such treatment and/or prophylaxis an effective amount of a compound of formula (I) or a pharmaceutically acceptable salt or solvate thereof.

Compounds of this invention and their preparation are illustrated in the following Examples, while the Descriptions illustrate the preparation of intermediates. Table I provides a summary of the intermediates and their preparation; Table 2 summarizes the structure of the products of the Examples.

The pharmacological activity of the compounds of this invention is illustrated using the following test procedures. The results are summarised in Table (III).

Description 1

1-ethoxycarbonyl pipecolic acid 15.0 g (0.116 moles) of (±) pipecolic acid were dissolved in 180 ml of water. 25.5 g (0.185 moles) of potassium carbonate were added and the solution cooled to +5° C. 19.83 g (0.183 moles) of ethyl chloroformate were added dropwise under mechanical stirring, maintaining the temperature below +10° C. After 4 hours the reaction mixture was extracted with methylene chloride; the aqueous layer were treated with conc. HCl to acidic pH, extracted with methylene chloride (400 ml) which was dried over $Na_2SO_4$ and the solvent evaporated to dryness to afford 23.8 g of the crude product. Crystallization from isopropyl ether/n-hexane gave 21.7 g (93% of the theoretical) of the title compound.

$C_9H_{15}NO_4$ M.W.=201.22 M.P.=82°-84° C. I.R. (KBr): 3100; 1760; 1650; 1445; 1275; 1195 $cm^{-1}$ N.M.R. ($CDCl_3$): δ7.2 (s, 1H); 4.9 (m, 1H); 4.2 (q, 2H); 4.0 80 MHz (m, 1H); 3.2-2.8 (m, 1H); 2.4-1.1 (m, 6H); 1.2 (t, 3H).

Description 1a (2S)-(3-pyrrolin-1-yl)carbonyl piperdine 4.5 ml (0.062 moles) of thionyl chloride were added dropwise to a stirred solution of 4.5 g (0.022 moles) of 1-ethoxycarbonyl-(S)-pipercolic acid in 60 ml of dry methylene chloride, cooled below −5° C. The stirring was continued 24 hours at room temperature and the solvent evaporated in vacuo to afford a residue which was dissolved in 30 ml of dry methylene chloride and added dropwise to a stirred solution of 3.3 g (0.048 moles) of 3-pyrroline in 40 ml of methylene chloride, cooled below −5° C. The stirring was continued 24 hours at room temperature; the reaction mixture was diluted with 50 ml of methylene chloride and washed twice with a saturated solution of $NaHCO_3$. The solvent was evaporated in vacuo to dryness to yield 3.0 g of the title compound, which was sufficiently pure for the following step.

Description 1b (2S)-(3-pyrrolin-1-yl)methyl piperidine 3.0 g (0.017 moles) of (2S)-(3-pyrrolin-1-yl)carbonyl piperidine were added dropwise, under nitrogen atmosphere, to a suspension of 1.2 g (0.031 moles) of lithium aluminium hydride in 60 ml of dry THF, at room temperature. After the addition was completed the slurry was heated 4 hours at 40° C. The alkaline work-up afforded 2.0 g of the title compound.

Description 2

1-(3-pyrrolin-1-yl)methyl-1,2,3,4-tetrahydroisoquinoline 3.33 g (0.032 moles) of 3-pyrroline hydrochloride were added, portionwise, at 0° C., to a solution of 1.64 g (0.041 moles) of NaOH in 30 ml of methanol. After 15′ 2.2 g (0.01 moles) of 1-chloromethyl-3,4-dihydroisoquinoline hydrochloride [J. Am. Chem. Soc. 59, 2555 (1933)] were added portionwise, under nitrogen, to the above stirred solution, cooled below −5° C.

The reaction mixture was stirred overnight at room temperature, heated 3 hours at 40° C. and then cooled to 0° C.; 1 g (0.026 moles) of sodium borohydride was added. After three hours 2 ml of conc. NaOH solution were added and the inorganic salts filtered off. The filtrate was concentrated in vacuo to afford a residue which was treated with conc. NaOH solution and exhaustively extracted with diethyl ether. The ethereal solution was filtered over celite, dried over $Na_2SO_4$ and the solvent evaporated in vacuo to dryness. The crude product was purified by silica gel flash column chromatography, eluting with a mixture of $CH_2Cl_2/MeOH/32\%$ $NH_4OH$, 94:5:0.5, to yield 1.4 g of the title compound.

In table I are summarized the structures, synthetic descriptions and analytical data of the intermediate diamines.

dropwise to a stirred solution of 1.0 g (6.02 mmoles) of 2(S)-(3-pyrrolin-1-yl)methyl piperidine dissolved in 30 ml of dry chloroform in the presence of 0.83 g (6.02 mmoles) of anhydrous potassium carbonate, kept at 0° C. The reaction mixture was stirred three hours at room temperature, washed with water, 5% NaOH solution and dried over $Na_2SO_4$; the solvent was evaporated in vacuo to dryness to afford 1.6 g of the crude product which was dissolved in 40 ml of ethyl acetate and the solution brought to acidic pH with HCl diethyl ether. The precipitate was filtered, washed and dried, to yield 1.1 g of the title compound.

$C_{18}H_{22}Cl_2N_2O\cdot HCl$  M.P.=211°–213° C. M.W.=389.751 I.R. (KBr) 3450; 2520; 1630 cm$^{-1}$ $[\alpha]_D^{20} = -43.8$ (C=1, MeOH)

EXAMPLE 2

TABLE I

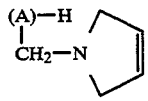

| (A)— | MOLECULAR FORMULA | SYNTHETIC DESCRIPTION | N.M.R. (CDCl$_3$)* 80 Mhz. |
|---|---|---|---|
| 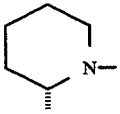 | $C_{10}H_{18}N_2$ | 1a, 1b | 5.8(s, 2H); 3.5(m, 4H); 2.9–3.2(m, 1H); 2.5–2.7(m, 2H); 2.2–2.4(m, 3H); 0.9–1.7(m, 6H) |
| 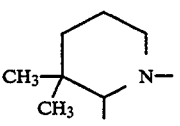 | $C_{12}H_{22}N_2$ | 1a, 1b | 5.8(s, 2H); 3.4(m, 4H); 2.9–3.2(m, 1H); 2.5–2.7(m, 2H); 2.2–2.4(m, 2H); 2.2(s, 1H); 0.9–1.7(m, 4H); 0.8(2d, 6H) |
| 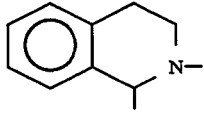 | $C_{14}H_{18}N_2$ | 2 | 7.0–7.2(m, 4H); 5.8(s, 2H); 4.0(dd, 1H); 3.5(s, 4H); 2.8–3.2(m, 6H); 2.7(s, 1H) |
| 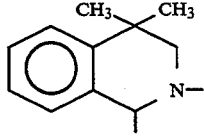 | $C_{16}H_{22}N_2$ | 2 | 7.0–7.2(m, 4H); 5.8(s, 2H); 4.0(dd, 1H); 3.5(s, 4H); 2.9–3.1(m, 4H); 2.6(s, 1H); 1.3(2d, 6H) |
| 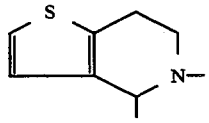 | $C_{12}H_{16}N_2S$ | 2 | 6.9(AB system, J=5Hz, 2H); 5.8(s, 2H); 3.9(dd, 1H); 3.5(s, 4H); 2.7–3.2(s, 6H); 2.4(s, 1H) |
| 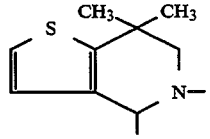 | $C_{14}H_{20}N_2S$ | 2 | 7.0(AB system, J=5Hz, 2H); 5.8(s, 2H); 3.9(dd, 1H); 3.5(s, 4H); 2.8–3.1(m, 4H); 2.5(s, 1H); 1.4(2d, 6H) |

*Data are given for the crude products, which were sufficiently pure for the subsequent reaction.

EXAMPLE 1

(2S)-1-(3,4-dichlorophenyl)acetyl-2-(3-pyrrolin-1-yl)methyl piperidine hydrochloride 1.6 g (7.15 mmoles) of 3,4-dichlorophenylacetyl chloride, dissolved in 10 ml of dry chloroform, were added 1-(3,4-dichlorophenyl)acetyl-2-(3-pyrrolin-1-yl)methyl-3,3-dimethyl piperidine hydrochloride Prepared as Example No. 1 from 0.50 g (2.77 moles) of 2-(3-pyrrolin-1-yl)methyl-3,3-dimethyl piperidine, 0.28 g (2.9 mmoles) of anhydrous potassium carbonate and 0.64 g (2.9 mmoles) of 3,4-dichlorophenylacetyl chloride in 25 ml of dry chloroform. The work-up afforded 0.65 g of a brown oil which was dissolved in 20 ml of ethyl acetate and the solution brought to acidic pH with HCl diethyl ether. The precipitate was filtered, washed and dried, to yield 0.20 g of the title compound. $C_{20}H_{26}Cl_2N_2O.HCl$ M.P.=223°-224° C. M.W.=417.803 Elemental analysis: Calcd. C,57.49; H,6.11; N,6.70; Cl,25.45; Found C,57.39; H,6.08; N,6.68; Cl,25.51. I.R. (KBr): 3450; 2950; 2520; 1630; 1470; 1430 cm$^{-1}$ N.M.R. (CDCl$_3$): δ12.0–12.6 (s, broad, 1H); 7.3–7.55 (m, 3H); (80 MHz) 5.85 (s, 2H); 4.7–5.1 (m, 2H); 2.8–4.7 (m, 9H); 1.2–1.7 (m, 4H); 0.9 (ds, 6H).

EXAMPLE 3

1-(4-trifluoromethylphenyl)acetyl-2-(3-pyrrolin-1-yl)methyl-3,3-dimethyl piperidine hydrochloride Prepared as Example No. 1 from 0.50 g (2.77 moles) of 2-(3-Pyrrolin-1-yl)methyl-3,3-dimethyl piperidine, 0.28 g (2.9 mmoles) of anhydrous potassium carbonate and 0.65 g (2.9 mmoles) of 4-trifluoromethylphenylacetyl chloride in 25 ml of dry chloroform. The work-up afforded 0.7 g of a brown oil which was dissolved in 20 ml of ethyl acetate and the solution brought to acidic pH with HCl diethyl ether. The precipitate was filtered, washed and dried, to yield 0.30 g of the title compound. $C_{21}H_{27}F_3N_2O$. HCl M.P.=250°-252 C. M.W.=416.907 Elemental analysis: Calcd. C,60.49; H,6.76; N,6.71; Cl,8.50; Found C,60.10; H,6.70; N,6.65; Cl,8.46. I.R. (KBr): 3440; 2955; 2560; 1625; 1430; 1340 cm$^{-1}$ N.M.R. (CDCl$_{13}$): δ12.1–12.7 (s, broad, 1H); 7.4–7.7 (m, 4H); (80 Mz) 5.8 (s, 2H); 4.7–5.1 (m, 2H); 2.8–4.6 (m, 9H); 1.2–1.7 (m, 4H); 0.9 (ds, 6H).

EXAMPLE 4

1-(5,6,7,8-tetrahydronapht-2-yl)acetyl-2-(3-pyrrolin-1-yl) methyl-3,3-dimethyl piperidine hydrochloride 1.43 g (6.97 mmoles) of dicyclohexylcarbodiimide, dissolved in 10 ml of dry chloroform, were added dropwise to a stirred solution of 0.6 g (3.3 mmoles) of 2-(3-pyrrolin-1-yl)methyl-3,3-dimethyl piperidine and 0.76 g (3.9 moles) of 5,6,7,8-tetrahydronapht-2-yl acetic acid in 20 ml of dry chloroform at −10° C. After the addition, the solution was allowed to reach room temperature and stirring continued overnight. The precipitate was filtered off and the filtrate was evaporated in vacuo to dryness. The residue was dissolved in 30 ml of ethyl acetate and washed with 10% NaOH. The organic layer was dried over sudium sulphate and evaporated in vacuo to dryness. The oily residue was taken up in 30 ml of ethyl acetate and brought to acidic pH with HCl/diethyl ether. The precipitate was filtered, washed and dried, to yield 0.35 g of the title compound. $C_{24}H_{34}N_2O.HCl$ M.P.=194°-196° C. M.W.=402.993 Elemental analysis: Calcd. C, 71.52; H, 8.75; N, 6.95; Found C, 71.40; H, 8.71; N, 6.88. I.R. (KBr): 3420; 2920; 2680; 1625; 1420 cm$^{-1}$ N.M.R. (CDCl$_3$): δ11.9–12.5 (s, broad, 1H); 6.9–7.1 (m, 3H); (80 MHz) 5.8 (s, 2H); 4.2–5.2 (m, 3H); 2.5–4.1 (m, 8H); 1.5–2.0 (m, 6H);1.0–1.5 (m, 6H); 0.9 (ds, 6H).

EXAMPLE 5

1-(3-pyrrolin-1-yl)methyl-2-(3,4-dichlorophenyl)acetyl-1,2,3,4-tetrahydroisoquinoline hydrochloride Prepared as Example No. 1 from 1.44 g (6.73 mmoles) of 1-(3-pyrrolin-1-yl)methyl-1,2,3,4-tetrahydroisoquinoline, 1.8 g (13.05 mmoles) of anhydrous potassium carbonate and 1.8 g (8.05 mmoles) of 3,4-dichlorophenylacetyl chloride in 50 ml of dry chloroform. The work-up of the reaction mixture afforded 1.9 g of the crude product which was dissolved in 60 ml of ethyl acetate and the solution brought to acidic pH with HCl/diethyl ether. The precipitate was filtered, washed and dried, to yield 1.5 g of the title compound.

$C_{22}H_{22}Cl_2N_2O$. HCl M.P.=256°-258° C. M.W.=437.791 Elemental analysis: Calcd. C,60.35; H,5.30; N,6.40; Cl,24.30; Found C,60.17; H,5.33; N,6.38; Cl,24.26. I.R. (KBr): 3450; 2550; 1625; 1450 cm$^{-1}$ N.M.R. (CDCl$_3$): δ12.5 (s, broad, 1H); 7.0–7.4 (m, 7H); (80 MHz) 6.1 (dd, 1H); 5.8 (s, 2H); 3.0–5.1 (m, 10H); 2.7–2.9 (m, 2H).

EXAMPLE 6

1-(3-pyrrolin-1-yl)methyl-2-(3,4-dichlorophenyl)acetyl-4,4-dimethyl-1,2,3,4-tetrahydroisoquinoline hydrochloride Prepared as Example No. 1 from 1.4 g (5.78 mmoles) of 1-(3-pyrrolin-1-yl)methyl-4,4-dimethyl-1,2,3,4-tetrahydroisoquinoline, 1.6 g (11.59 moles) of anhydrous potassium carbonate and 1.5 g (6.71 moles) of 3,4-dichlorophenylacetyl chloride in 50 ml of dry chloroform. The work-up of the reaction mixture afforded 1.9 g of the crude product which was dissolved in 60 ml of ethyl acetate and the solution brought to acidic pH with HCl/diethyl ether. The precipitate was filtered, washed and dried, to yield 1.6 g of the title compound. $C_{24}H_{26}Cl_2N_2O.HCl$ M.P.=254°-257° C. M.W.=465.843 Elemental analysis: Calcd. C,61.87; H,5.84; N,6.01; Cl,22.83; Found C,61.94; H,5.88; N,5.99; Cl,22.75. I.R. (KBr): 3450; 2960; 2540; 1630; 1440 cm$^{-1}$ N.M.R. (CDCl$_3$): δ12.5 (s, broad, 1H); 6.9–7.5 (m, 7H); (80 MHz) 6.1 (dd, 1H); 5.8 (s, 2H); 3.9–5.1 (m, 4H); 3.0–3.9 (m, 6H); 1.4 (s, 3H); 1.2 (s, 3H).

EXAMPLE 7

4-(3-pyrrolin-1-yl)methyl-5-(3,4-dichlorophenyl)acetyl-4,5,6,7-tetrahydrothieno[3,2-c]pyridine hydrochloride hemihydrate Prepared as Example No. 1 from 0.38 g (1.72 mmoles) of 4-(3-pyrrolin-1-yl)methyl-4,5,6,7-tetrahydrothieno[3,2-c]pyridine, 0.47 g (3.40 mmoles) of anhydrous potassium carbonate and 0.46 g (2.05 moles) of 3,4-dichlorophenylacetyl chloride in 20 ml of dry chloroform. The work-up of the reaction mixture afforded 0.51 g of the crude product which was purified by flash column chromatography eluting with ethyl acetate containing 0.2% of 32% NH$_4$OH solution to give 0.40 g of the pure product. This was dissolved in 20 ml of ethyl acetate and the solution brought to acidic pH with HCl/diethyl ether. The precipitate was filtered, washed and dried, to yield 0.35 g of the title compound.

$C_{20}H_{20}Cl_2N_2OS.HCl.\frac{1}{2}H_2O$ M.P.=238°-240° C. M.W.=452.829 Elemental analysis: Calcd. C, 53.04; H, 4.89; N, 6.18; Cl, 23.49; S, 7.08; Found C, 52.44; H, 4.79; N, 6.06; Cl, 23.21; S, 7.02; I.R. (KBr): 3450; 2520; 1640; 1440 cm$^{-1}$

EXAMPLE 8

4-(3-pyrrolin-1-yl)methyl-5-(3,4-dichlorophenyl)acetyl-7,7-dimethyl-4,5,6,7-tetrahydrothieno[3,2-c]pyridine hydrochloride Prepared as Example No. 1 from 1.18 g (4.76 mmoles) of 4-(3-pyrrolin-1-yl)methyl-7,7-dimethyl-4,5,6,7-tetrahydrothieno[3,2-c]pyridine, 1.30 g (9.42 mmoles) of anhydrous potassium carbonate and 1.16 g (5.19 mmoles) of 3,4-dichlorophenylacetyl chloride in 50 ml of dry chloroform. The work-up of the reaction mixture afforded 2.2 g of the crude product which was purified by flash column chromatography eluting with a mixture of ethyl acetate/hexane/32% NH$_4$OH, 70:30:0.2 to give 1.1 g of the pure product. This was dissolved in 40 ml of ethyl acetate and the solution brought to acidic pH with HCl/diethyl ether. The precipitate was filtered, washed and dried, to yield 0.70 g of the title compound.

$C_{22}H_{24}Cl_2N_2OS.HCl$   M.P.=174°–175° C. M.W.=471.873 I.R. (KBr): 3420; 2520; 1645; 1435: 1410 cm$^{-1}$ N.M.R. (CDCl$_3$): δ12.50 (s broad, 1H); 7.25–7.45 (m, 3H); (80 MHz) 6.95 (AB system, J=5.27 Hz, 2H); 6.12 (dd, J1=10.83 Hz, J2=3.51 Hz, 1H); 5.82 (s, 2H); 4.32–5.06 (m, 3H); 2.98–4.23 (m, 7H); 1.42 (s, 3H); 1.28 (5, 3H).

EXAMPLE 9

(2S)-1-[1-oxo-3,4-dihydro-(2H)-napht-6-yl]acetyl-2-(3-pyrrolin-1-yl)methyl piperidine hydrochloride Prepared as Example No. 1 from 1.8 g (10.8 mmoles) of (2S)-(3-pyrrolin-1-yl)methyl piperidine, 3.0 g (21.74 mmoles) of anhydrous potassium carbonate and 2.6 g (11.68 moles) of 1-oxo-3,4-dihydro-(2H)-napht-6-yl acetyl chloride in 50 ml of dry chloroform. The work-up of the reaction mixture afforded 3.8 g of the crude product which was purified by flash column chromatography eluting with a mixture of CH$_2$Cl$_2$/MeOH/32% NH$_4$OH 94:5:0.5 to give 1.6 g of the pure product. This was dissolved in 40 ml of acetone and the solution brought to acidic pH with HCl/diethyl ether. The precipitate was filtered, washed and dried, to yield 1.2 g of the title compound.

$C_{22}H_{28}N_2O_2.HCl$   M.P.=199°–201° C. M.W.=388.925 Elemental analysis: Calcd. C,67.94; H,7.52; N,7.20; Cl,9.12; Found C,67.55; H,7.60; N,7.09; Cl,9.06; I.R. (KBr): 3450; 2940; 2520; 1680; 1635; 1607; 1435 cm$^{-1}$ []$_D^{20}$=−40.2 (C=1, MeOH)

EXAMPLE 10

1-[1-oxo-3,4-dihydro-(2H)-napht-6-yl]acetyl-2-(3-pyrrolin-1-yl)methyl-3,3-dimethyl piperidine hydrochloride.

Prepared as described in Example No. 1, from 1.50 g (5.6 mmoles) of 2-(3-pyrrolin-1-yl)methyl-3,3-dimethyl piperidine dihydrochloride, 1.54 g (11.2 mmoles) of anhydrous potassium carbonate and 1.37 g (6.16 mmoles) of [1-oxo-3,4-dihydro-(2H)-napht-6-yl]acetyl chloride in 40 ml of dry chloroform. The work-up of the reaction mixture afforded 1.10 g of the crude product which was purified by flash column chromatography eluting with a mixture of CH$_2$Cl$_2$/ MeOH/32% NH$_4$OH 94:5:0.5 to give 250 mg of the pure product. This was dissolved in 20 ml of acetone and the solution brought to acidic pH with HCl/diethyl ether. The precipitate was filtered, washed and dried, to yield 120 mg of the title compound. $C_{24}H_{32}N_2O_2.HCl$ M.P.=221°–224° C. M.W.=416.977 Elemental analysis: Calcd. C,69.13; H,7.98; N,6.72; Cl,8.50; Found C,69.00; H,7.87; N,6.70; Cl,8.45. I.R. (KBr): 3450; 2950; 1680; 1625; 1610; 1425 cm$^{-1}$

TABLE II

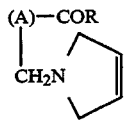

| Example | (A)— | R | MOLECULAR FORMULA | MELTING POINT (°C.) |
|---|---|---|---|---|
| 1 | piperidine N— (with stereo) | —CH$_2$—C$_6$H$_3$(Cl)(Cl) | $C_{18}H_{22}Cl_2N_2O.HCl$ | 211–213 |
| 2 | 3,3-dimethyl piperidine N— | —CH$_2$—C$_6$H$_3$(Cl)(Cl) | $C_{20}H_{26}Cl_2N_2O.HCl$ | 223–224 |
| 3 | 3,3-dimethyl piperidine N— | —CH$_2$—C$_6$H$_4$—CF$_3$ | $C_{21}H_{27}F_3N_2O.HCl$ | 250–252 |
| 4 | 3,3-dimethyl piperidine N— | —CH$_2$—tetrahydronaphthyl | $C_{24}H_{34}N_2O.HCl$ | 194–196 |

TABLE II-continued

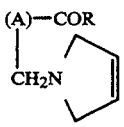

| Example | (A)— | R | MOLECULAR FORMULA | MELTING POINT (°C.) |
|---|---|---|---|---|
| 5 | [1,2,3,4-tetrahydroisoquinolinyl] | -CH2-(3,4-dichlorophenyl) | $C_{22}H_{22}Cl_2N_2O \cdot HCl$ | 256–258 |
| 6 | [4,4-dimethyl-1,2,3,4-tetrahydroisoquinolinyl] | -CH2-(3,4-dichlorophenyl) | $C_{24}H_{26}Cl_2N_2O \cdot HCl$ | 254–257 |
| 7 | [thienopyridinyl] | -CH2-(3,4-dichlorophenyl) | $C_{20}H_{20}Cl_2N_2OS \cdot HCl \cdot \tfrac{1}{2}H_2O$ | 238–240 |
| 8 | [dimethyl-thienopyridinyl] | -CH2-(3,4-dichlorophenyl) | $C_{22}H_{24}Cl_2N_2OS \cdot HCl$ | 174–175 |
| 9 | [piperidinyl] | -CH2-(tetralone) | $C_{22}H_{28}N_2O_2 \cdot HCl$ | 199–201 |
| 10 | [3,3-dimethylpiperidinyl] | -CH2-(tetralone) | $C_{24}H_{32}N_2O_2 \cdot HCl$ | 221–224 |

PHARMACOLOGICAL TESTS

A) P-phenylquinone-induced abdominal writhing test in mice

The methodology employed is based on that described by Sigmund et al, Proc. Soc. Exptl. Biol. 95, 729/1957, modified by Milne and Twomey, Agents and Actions, 10, 31/1980.

Male Charles River mice (Swiss Strain), 25–36 g body weight, were used. Animals were allowed food and water ad libitum and were randomized into groups of 10 prior to experimentation. Test compounds were dissolved in either distilled water or distilled water plus 0.1M AMS, and administered by the subcutaneous route in a final volume of 10 ml/Kg. Control animals received 10 ml/Kg of the appropriate vehicle alone. Following a pretreatment period of 20 min., mice were injected intraperitoneally with p-phenylquinone, 2 mg/Kg at 37° C. in a final volume of 10 mg/Kg. Next, the mice were placed, in groups of 3, in a compartmented perspex box maintained at room temperature and were observed for a period of 8 min. During this period the number of abdominal writhing responses per animal were recorded where writhing consists of an intermittent contraction of the abdomen associated with hind leg extension.

The degree of antinociceptive protection afforded by the test compound was determined as the mean number of writhing responses observed in the treated group (T) expressed as a percentage of the mean number of writhing responses in the control group (C) according to the following formula:

$$[1-(T/C)] \times 100\% = \% \text{ graded protection}$$

B) Tail-flick test in mice

The methodology employed is based on that described by D'Amour and Smith, J. Pharmacol. Exp. Ther. 72, 74/1941.

Male Charles River mice (Swiss Strain), 22–34 g body weight were used. Animals were allowed food and water ad libitum and were randomized into groups of 10 prior to experimentation. Before administration of the test compound, the reaction time of each animal was determined by focusing a beam of light onto the tail, eliciting a reflex withdrawal after a certain latency; only mice exhibiting a latency between 3–8 sec. were used subsequently in the evaluation of drug effects.

Test compounds were dissolved in either distilled water or distilled water plus 0.1M AMS and administered by the subcutaneous route in a final volume of 10 ml/Kg. Control animals received 10 ml/kg of the appropriate vehicle alone. Following a pretreatment period of 30 min., the mice were again placed under the heat source and the reaction tine re-determined.

Percentage quantal protection was determined as the number of mice in which the reaction time was doubled compared to pretreatment values, expressed as a percentage of the total number of mice in the group.

TABLE

| | ANALGESIA | |
|---|---|---|
| Example No | MOUSE WRITHING ED50 mg/kg s.c. | MOUSE TAIL-FLICK ED50 mg/kg s.c. |
| 1 | 0.005 | 0.045 |
| 2 | 0.006 | 0.021 |
| 3 | 0.006 | 0.015 |
| 4 | 0.025 | 0.193 |
| 5 | 0.005 | 0.015 |
| 6 | 0.047 | 0.275 |
| 7 | 0.002 | 0.008 |
| 8 | 0.040 | 0.550 |
| 9 | 0.023 | 0.316 |
| 10 | 0.053 | 0.594 |

We claim:

1. A compound, or a solvate or salt thereof, of the formula (I):

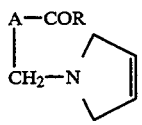    (I)

wherein

A is

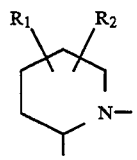

or

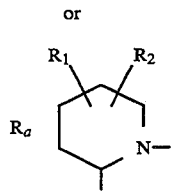

$R_1$ and $R_2$ are simultaneously hydrogen, or are both $C_{1-6}$alkyl groups on the same carbon atom;

$R_a$ comprises a substituted or unsubstituted phenyl or thienyl group; and

R is selected from

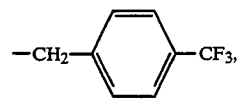

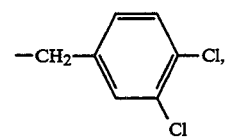

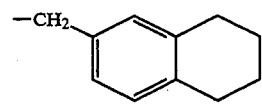

and

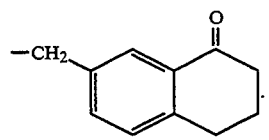

2. A compound according to claim 1 wherein R is

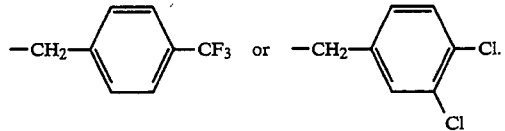

3. A compound according to claim 1 in which $R_1$ or $R_2$ is methyl, ethyl, propyl, n-butyl, n-pentyl or n-hexyl.

4. A compound according to claim 1 which is

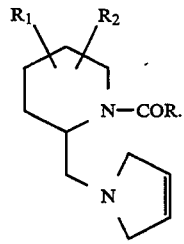

5. A compound to claim 4 wherein $R_1$ and $R_2$ are gem-dimethyl.

6. A compound according to claim 4 which is:
1-(3,4-dichlorophenyl)acetyl-2(3-pyrrolin-1-yl)methyl-3,3-dimethyl piperidine; or
1-(4-trifluoromethylphenyl)acetyl-2-(3-pyrrolin-1-yl)methyl-3,3-dimethyl piperidine.

7. A compound according to claim 1 which is

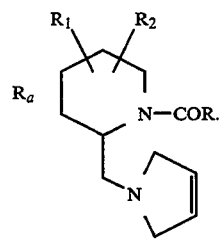

8. A compound according to claim 7 wherein $R_a$ comprise a phenyl ring.

9. A compound according to claim 7 wherein $R_a$ comprises a thieno ring.

10. A compound according to claim 7 which is 4-(3-pyrrolin-1-yl)methyl-5-(3,4-dichlorophenyl)acetyl-4,5,6,7-tetrahydrothieno[3,2-c]pyridine.

11. A compound according to claim 7 which is 1-(3-pyrrolin-1-yl)methyl-2-(3,4-dichlorophenyl) acetyl-1,2,3,4-tetrahydroisoquinoline.

12. A pharmaceutical composition comprising a compound according to claim 1 and a pharmaceutically acceptable carrier.

13. A method for the treatment of pain and/or hyponatraemic disease states and/or cerebral ischemia in mammals, which comprises administering to the mammal in need of such treatment an effective amount of a compound according to claim 1 or a pharmaceutically acceptable salt or solvate thereof.

* * * * *